United States Patent [19]

Kejha et al.

[11] Patent Number: 5,175,264
[45] Date of Patent: Dec. 29, 1992

[54] 5-[4-(4,6-DIMETHYL-2-PYRIMIDINYLSULFAMOYL)PHENYLAZO]ACETYLSALICYLIC ACID

[75] Inventors: Jiri Kejha; Bohumila Brunova; Darina Slukova; Miroslav Kuchar; Eva Knezova; Jaroslava Grimova, all of Prague, Czechoslovakia

[73] Assignee: Výzkumný ústav pro farmacii a biochemii, státní podnik, Czechoslovakia

[21] Appl. No.: 776,081

[22] Filed: Oct. 11, 1991

[30] Foreign Application Priority Data

May 15, 1991 [CS] Czechoslovakia .................... 1426-91

[51] Int. Cl.⁵ .................. C07C 245/08; A61K 31/665
[52] U.S. Cl. .................................................... 534/664
[58] Field of Search ........................................ 534/664

[56] References Cited

U.S. PATENT DOCUMENTS

| 2,396,145 | 3/1946 | Anders et al. | 534/664 |
| 2,665,273 | 1/1954 | Mast et al. | 534/664 |
| 3,681,319 | 8/1972 | Lindberg | 534/664 |
| 3,915,951 | 10/1975 | Agback et al. | 534/664 |
| 4,045,429 | 8/1977 | Agback | 534/664 X |
| 4,219,474 | 8/1980 | Zalipsky et al. | 534/664 |

FOREIGN PATENT DOCUMENTS 0166693  9/1950  Austria .................. 534/664

Primary Examiner—Floyd D. Higel
Attorney, Agent, or Firm—McGlew and Tuttle

[57] ABSTRACT

This invention relates to 5-[4-[-(4,6-dimethyl-2-pyrimidinylsulfamoyl)phenylazo]acetylsalicylic acid (DISALAZINE) is provided as a new compound having anti-arthritic and immunomodulating properties. It can be produced via reaction of the diazonium salt of sulfadimidine reacted with salicylic acid and then acetylating the product anti-arthritic and immunomodulating properties.

1 Claim, No Drawings

5-[4-(4,6-DIMETHYL-2-PYRIMIDINYLSULFAMOYL)PHENYLAZO]ACETYLSALICYLIC ACID

BACKGROUND OF THE INVENTION

The substance which is the subject of the invention is an analogue of a known therapeutic, namely sulfasalazine (i.e. 5-[4-(2-pyridysulfamoyl) phenylazo] salicylic acid) discovered in 1942 (Acta Medica Scandinavica 60, 1942, p. 577–598, N. Schwartz) and used in the therapy of progressive polyarthritis and ulcerative colitis. Sulfasalazine also influences various steps in the metabolism of arachidonic acid and has immunomodulating properties (J. Clin. Invest. 69, 1982, p. 494, W. R. Stenson). A shortcoming of this drug is its low biological availability and some unfavorable side effects. Therefore a series of analogues of sulfasalazine was synthesized with the aim to finding a substance of more favorable therapeutic and pharmacokinetic properties, especially a higher biological availability.

DESCRIPTION OF THE INVENTION

According to this invention, 5-[4-(4,6-dimethyl-2-pyrimidinylsulfamoyl) phenylazo] acetylasalicyclic acid hereinafter sondines referred to as DISALAZINE, of the following formula I

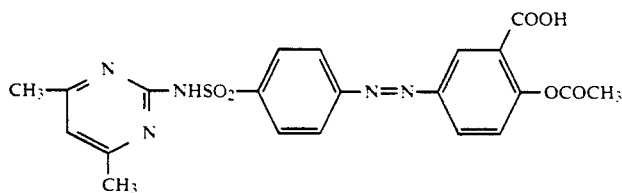

is provided its production being accomplished by first preparing the diazonium salt of sulfamidine (i.e. 4,6-dimethyl-2-sulfanilamidopyrimidine) by a known process and then allowing it to react at from $-2°$ C. to $+10°$ C. with salicyclic acid in an alkaline medium, e.g. sodium hydroxide, sodium carbonate and the like. The resulting product is precipitated by acidification and is collected on a filter. The product must be precipitated, e.g. from a $NaHCO_3$ solution, mainly to remove mechanical impurities as well as other extraneous products. For the acidification of the alkaline solution, it is advantageous to add ethyl acetate to precipitate the crystalline product. In the next step, acetylation of the hydroxy group is carried out with the aid of acetanhydride or acetylchloride, in the presence of toluene or acetic acid. Otherwise the diazonium salt of sulfadimidine can be reacted directly with acetylsalicylic acid in alkaline medium. The resulting product precipitates upon acidification and is collected on a filter.

Experimentally the substance has a significant antiarthritic and immunomodulating activity, low toxicity, and three times greater biological availability in comparison with sulfasalazine.

MODE OF EXPLOITATION

It is possible to use the instant substance i.e. Disalazine as a therapeutic drug with antiarthritic and immunomodulating activity.

The antiarthritic activity of DISALAZINE was tested in comparison with sulfasalazine in a model of rate adjuvant disease with preventive administration. The clinical symptoms of disease (oedema of limbs, osteous lesions, articular motility, body weight), as well as their influence on the immunological functions were evaluated. DISALAZINE significantly diminished the size of limb oedema and the extent of osteous injury, and increased the articular motility and the body weight. In all instances, DISALAZINE gave better results than sulfasalazine (Table 1).

TABLE 1

| Antiarthritic activity of DISALAZINE (dose 400 mg/kg)% | | | | |
|---|---|---|---|---|
| | body weight | limb oedema | articular motility | osteous lesions |
| Healthy rats | 100 | 0 | 100 | 0 |
| Non-medicated rats | 35 | 100 | 31 | 100 |
| Medicated rats by: | | | | |
| DISALAZINE | 68 | 52 | 80 | 27 |
| sulfasalazine | 37 | 57 | 53 | 66 |

Neither DISALAZINE nor sulfasalazine in the dose of 400 mg/kg affected the number of exudate cells in the model of experimental pleuritis. The phagocytic activity (the number of phagocyting cells) measured on the model of phagocytosis of peritoneal macrophages was significantly reduced by DISALAZINE (49.6% of control) like sulfasalazine (54,7% of control), both in 400 mg/kg: the cellularity of exudate was reduced to 55% of control, similarly as the number of glass adherent cells (52% of control).

The immunosupression induced by azathioprine was significantly inhibited by DISALAZINE after multiple doses of 100 mg/kg. DISALAZINE showed expressive in vitro effect on lymphocyte proliferation induced by Con A. In comparison with sulfasalazine which had low effect, DISALAZINE in the concentration range 40 μg to 4 pg significantly stimulated lymphocyte proliferation. The stimulation of LPS induced proliferation of lymphocytes was milder and comparable with sulfasalazine.

The synthesis of LT $B_4$ was not affected by DISALAZINE in rat pleural PMNL.

Pharmacokinetic studies with labelled substances show that DISALAZINE in comparison with sufasalazine is substantially better resorbed, has a longer half-life of elimination and maximum blood levels are attained about 12 hours after administration.

The main advantage of the insant substance disalazine is its experimentally proven significant anti-arthritic and immunomodulating activity and low toxicity. These properties give promise for its exploitation in clinical practice especially in the therapy of progressive polyarthritis. (See Table 2).

Details of the synthesis are obvious from the following examples which illustrate but do not in the least limit the whole process.

EXAMPLE 1

50 g 4.6-dimethyl-2-sulfanilamidopyrimidine are dissolved in 250 ml water and 45 ml concentrated hydrochloric acid. The solution is cooled to 0° c.-5° C. and a solution of 12 g NaNO₂ in 50 ml water is added dropwise. It is stirred for 1 hour further at the same temperature and the solution of the resulting diazonium salt is then slowly added to 25.2 salicylic acid dissolved in a solution of 30 g NaOH and 250 ml water. The resulting red-brown solution is then stirred for 30 minutes. Afterwards, 300 ml ethyl acetate are is added and under intensive stirring 70 ml 1:1 diluted hydrochloric acid is added dropwise. The precipitated substance is collected on a filter and dried at 110° C. 70.4 g, i.e. 91.6% of theory, of 5-[4-(4,6-dimethyl-2-pyrimidinylsulfamoyl) phenylazo] salicyclic acid, having a melting point of 226° C.-231° C. are isolated.

EXAMPLE 2

85.5 g 5-[4-(4,6-dimethyl-2-pyrimidinylsulfamoyl) phenylazo] salicyclic acid are dissolved in a solution prepared by dissolving 33.6 g NaHCO₃ in 100 ml water. The resulting alkaline aqueous solution is extracted with 250 ml ethyl acetate. The water phase is filtered with charcoal and after the addition of 366 ml of ethyl acetate, the alkaline solution is acidified with hydrochloric acid diluted 1:1 until and acid reaction is obtained. The precipitated product is collected on a filter and washed in water. 82.8 g refined (purified) 5-[4-(4,6-dimethyl-2-pyrimidinylsulfamoyl) phenylazo] salicyclic acid m.p. of 228°-230° C. are isolated.

EXAMPLE 3

20 g 5-[4-(4,6-dimethyl-2-pyrimidinylsulfamoyl) phenylazo] salicylic acid are suspended in a mixture of 10 ml acetanhydride, 20 ml acetic acid, and 0.05 g concentrated sulphuric acid. The reaction mixture is heated to 130° C.-150° C. and stirred at this temperature for 2 hour. Upon cooling to 100° C., 20 ml toluene are added and stirring continues for a further 1 hour. After cooling, the precipitated product is collected on a filter and dried at 110° C.-120° C. 17.5 g 5-[4-(4,6-dimethyl-2-pyrimidinylsulfamoyl) phenylazo] salicylic acid, (formula I) i.e. 80% of theory, having a melting point of 185° C.-187° C. (decomposed) is isolated. The structure of the recovered substance has been confirmed by emission absorbance (EA) and NMR.

EXAMPLE 4

11.6 g 4,6-dimethyl-2-sulfanilamidopyrimidine are dissolved in a mixture of 140 ml water and 11 ml concentrated hydrochloric acid, the solution is cooled to 0° C.-5° C. and within 20 minutes 3 g NaNO₂ in 140 ml water are added dropwise. The solution is stirred further for 1 hour at the same temperature. The and the solution of the resulting diazonium salt is then slowly poured into a solution of 7.7 g acetylsalicyclic acid in 220 ml water and 10.7 g sodium hydroxide cooled to 10° C. The reaction mixture is stirred further for 3 hour at room temperature. Precipitated crystals of the sodium salt are collected on a filter. Still moist, they are dissolved in 200 ml water and the solution is acidified with hydrochloric acid. The precipitate is collected on a filter, washed 5 times in 100 ml water and dried at 110° C.-120° C. 12.3 g, i.e. 62.9% of theory, of 5-[4-(4,6-dimethyl-2-pyrimidinylsulfamoyl) phenylazo] salicylic acid, having a with melting point of 186° C. (decomposed) are isolated.

EXAMPLE 5

21.4 g 5-[4-(4,6-dimethyl-2-pyrimidinylsulfamoyl) phenylazo] salicylic acid are is suspended in a mixture of 13.27 g acetanhydride and 17.1 ml toluene. The reaction mixture is heated under stirring 5 hours. After cooling to 20° C. the solid fraction is filtered and washed with toluene. After drying 21.3 g are obtained of 5-[4-(4,6-dimethyl-2-pyrimidinylsulfamoyl) phenylazo] salicylic acid, i.e. 90.6% of theory, which is recrystallized from acetanhydride in a yield of 75-80% of theory.

We claim:

1. 5-[4-(4,6-dimethyl-2-pyrimidinylsulfamoyl/-phenylazo] acetylsalicylic acid, of the formula

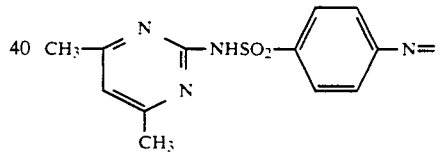

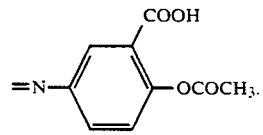

* * * * *